United States Patent

Assmann et al.

[11] Patent Number: 6,090,831
[45] Date of Patent: Jul. 18, 2000

[54] USE OF SULFONYLOXADIAZOLONES AS MICROBICIDES

[75] Inventors: Lutz Assmann, St. Peter-Ording; Peter Gerdes, Aachen; Klaus Stenzel, Düsseldorf, all of Germany

[73] Assignee: Bayer Aktiengesellschaft, Leverkusen, Germany

[21] Appl. No.: 09/403,207

[22] PCT Filed: Apr. 6, 1998

[86] PCT No.: PCT/EP98/01988

§ 371 Date: Oct. 14, 1999

§ 102(e) Date: Oct. 14, 1999

[87] PCT Pub. No.: WO98/47369

PCT Pub. Date: Oct. 29, 1998

[30] Foreign Application Priority Data

Apr. 18, 1997 [DE] Germany .......................... 197 16 259

[51] Int. Cl.$^7$ .................................................. A01N 43/82
[52] U.S. Cl. ..................... 514/364; 548/132; 546/269.1
[58] Field of Search ........................... 548/132; 514/364; 546/269.1

[56] References Cited

U.S. PATENT DOCUMENTS 3,994,909 11/1976 Pommer et al. ...................... 260/302 D
4,420,486 12/1983 Ohyama et al. ......................... 424/272

OTHER PUBLICATIONS

Database WPI, Section Ch, Week 8722, Derwent Publications Ltd., London, GB; Class C02, AN 87–154900, XP002073605 –& JP 62 093 283 A (Idemitsu Kosan Co Ltd) siehe Zusammenfassung.
Zh. Org. Khim., 27, 1991, A.A. Ecunehko et al, pp. 1262–1270.
Synthesis, Jun. 6, 1983, Editors G. Schill, G. Sosnovsky and H.J. Ziegler, Communications pp. 483–486.
J. Heterocyclic Chem., Jun. 10, 1973, pp. 357–362, Synthesis of 4(5)–Substituted 2–Amino–5(4)–Hydroxyimino–5(4)H–imidazoles and Their Transformation into the Corresponding 3–Substituted 5–Amino–1,2,4–oxadiaoles, Bruno Cavalleri etal.
Journal of Organic Chemistry, vol. 41, Sep.–Dec. 1976, pp. 3233–3237, Babu George et al, Heterocycles from N–Ethoxycarbonylthioamides and Einucleophilic Reagents, 1. Dihydro–1,2,4–triazolones and 1,2,4–Oxadiazolones.
J. Heterocyclic Chem., 30, (5), Oct.–Nov. 1993, pp. 1253–1260, Heterocyclic Amino Acids as Synthons, Reactions with Dicarbonyl Compounds, Patrik Kolar et al.
J. Heterocyclic Chem., Aug. 1981, pp. 997–1006, Some Heterocyclic Sulfonyl Chlorides and Derivative, kRichard J. Cremlyn et al.

Primary Examiner—Robert Gerstl
Attorney, Agent, or Firm—Joseph C. Gil

[57] ABSTRACT

Sulphonyloxadiazolones of the formula

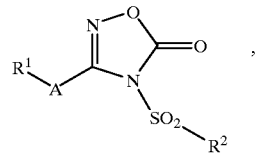
(I)

in which
A represents a single bond or represents alkanediyl, alkenediyl, alkinediyl or a grouping —*O—CH$_2$—, —*O—CH$_2$—CH$_2$—, —*CH$_2$—O—, —*CH$_2$—O—CH$_2$—CH$_2$—, —*CH$_2$—S—, —*S—CH$_2$—,

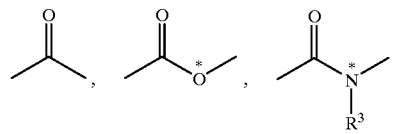

or

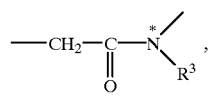

where the atom labelled by * is in each case attached to $R^1$ and
$R^3$ represents hydrogen or alkyl,
$R^1$ represents hydrogen, optionally substituted cycloalkyl, optionally substituted cycloalkenyl, optionally substituted aryl or optionally substituted heterocyclyl and
$R^2$ represents in each case optionally substituted alkyl, alkenyl, dialkylamino, aryl or heterocyclyl,
are highly suitable for controlling undesirable microorganisms in crop protection and in the protection of materials.
Novel sulphonyloxadiazolones of the formula

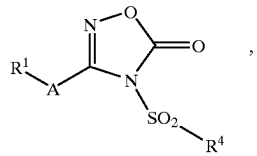
(Ia)

in which
A and $R^1$ are as defined above and
$R^4$ represents optionally substituted alkyl, optionally substituted alkenyl, dialkylamino, nitro-substituted phenyl which may also contain one or two further substituents, or represents optionally substituted heterocyclyl, but where $R^4$ does not represent propyl if A represents a direct bond and $R^1$ represents 2,4,5-trimethyl-phenyl,
and a process for preparing these substances.

8 Claims, No Drawings

USE OF SULFONYLOXADIAZOLONES AS MICROBICIDES

The present invention relates to the use of sulphonyloxadiazolones, some of which are known, as microbicides in crop protection and in the protection of materials. Moreover, the invention also relates to novel sulphonyloxadiazolones and to a process for their preparation.

Certain sulphonyloxadiazolones, such as, for example, 4-[(4-chlorophenyl)-sulphonyl]-3-(2,4,6-trimethylphenyl)-1,2,4-oxadiazol-5(4H)-one, are already known (cf. Zh. Org. Khim. 27 (1991), 1262–1270). However, a biological action of these compounds has hitherto not been described.

It has now been found that sulphonyloxadiazolones of the formula

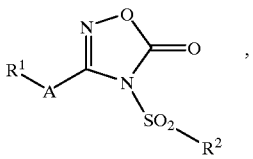

(I)

in which
A represents a single bond or represents alkanediyl, alkenediyl, alkinediyl or a grouping —*O—CH$_2$—, —*O—CH$_2$—CH$_2$—, —*CH$_2$—O—, —*CH$_2$—O—CH$_2$—CH$_2$—, —*CH$_2$S—, —*S—CH$_2$—,

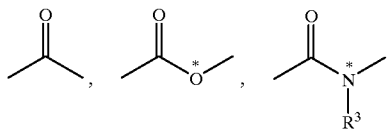

or

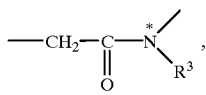

where the atom labelled by * is in each case attached to R$^1$ and
R$^3$ represents hydrogen or alkyl,
R$^1$ represents hydrogen, optionally substituted cycloalkyl, optionally substituted cycloalkenyl, optionally substituted aryl or optionally substituted heterocyclyl and
R$^2$ represents in each case optionally substituted alkyl, alkenyl, dialkylamino, aryl or heterocyclyl,
are highly suitable for controlling undesirable microorganisms in crop protection and in the protection of materials.

Surprisingly, the sulphonyloxadiazolones of the formula (I) to be used according to the invention show considerably better activity against undesirable microorganisms, in particular fungi, than the constitutionally most similar prior-art substances of the same direction of action.

The formula (I) provides a general definition of the substances to be used according to the invention.

Heterocyclyl represents cyclic compounds in which at least one ring member is a heteroatom, i.e. an atom different from carbon. If the ring contains a plurality of heteroatoms, these can be identical or different. Preferred heteroatoms are oxygen, nitrogen or sulphur. If the ring contains a plurality of oxygen atoms, these are not adjacent.

A preferably represents a single bond or represents alkanediyl having 1 to 4 carbon atoms, alkenediyl having 2 to 4 carbon atoms, alkinediyl having 2 to 4 carbon atoms or a grouping —*O—CH$_2$—, —*O—CH$_2$—CH$_2$—, —*CH$_2$—O—, —*CH$_2$—O—CH$_2$—CH$_2$—, —*CH$_2$—S—, —*S—CH$_2$—,

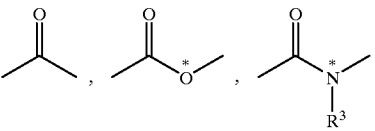

or

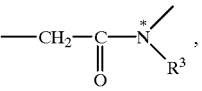

where the atom labelled by * is in each case attached to R$^1$.
R$^3$ preferably represents hydrogen or alkyl having 1 to 4 carbon atoms.
R$^1$ preferably represents hydrogen, or represents cycloalkyl having 3 to 8 carbon atoms or cycloalkenyl having 3 to 8 carbon atoms, each of which is optionally mono- to trisubstituted by identical or different substituents from the group consisting of halogen and alkyl having 1 to 3 carbon atoms.
R$^1$ furthermore preferably represents aryl having 6 to 10 carbon atoms, where each of these radicals may be mono- to trisubstituted by identical or different substituents from the group consisting of
halogen, nitro, carbamoyl;
in each case straight-chain or branched alkyl, alkoxy, alkylthio or alkylsulphonyl having in each case 1 to 6 carbon atoms;
in each case straight-chain or branched alkenyl or alkenyloxy having in each case 2 to 6 carbon atoms;
in each case straight-chain or branched halogenoalkyl, halogenoalkoxy, halogenoalkylthio or halogenoalkylsulphonyl having in each case 1 to 6 carbon atoms and 1 to 5 identical or different halogen atoms;
in each case straight-chain or branched halogenoalkenyl or halogenoalkenyloxy having in each case 2 to 6 carbon atoms and 1 to 5 identical or different halogen atoms;
in each case straight-chain or branched alkylamino, dialkylamino, alkylcarbonyl, alkoxycarbonyl, hydroxyiminoalkyl or alkoximinoalkyl having in each case 1 to 6 carbon atoms in the individual alkyl moieties;
in each case doubly attached alkylene or dioxyalkylene having in each case 1 to 6 carbon atoms and being in each case optionally mono- to tetrasubstituted by identical or different substituents from the group consisting of halogen, straight-chain or branched alkyl having from 1 to 4 carbon atoms and straight-chain or branched halogenoalkyl having 1 to 4 carbon atoms and 1 to 5 identical or different halogen atoms;
cycloalkyl having 3 to 6 carbon atoms;
and
aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, where these aromatic or heterocyclic radicals may be mono- to trisubstituted by identical or different substituents from the group consisting of halogen, nitro, straight-chain or branched alkyl having 1 to 4 carbon atoms, straight-chain or branched halogenoalkyl having 1 to 4 carbon atoms and 1 to 5 identical or different halogen atoms, straight-chain or branched alkoxy or alkylthio having 1 to 4 carbon atoms, and straight-chain or branched halogenoalkoxy having 1 to 4 carbon atoms and 1 to 9 identical or different halogen atoms.

$R^1$ moreover preferably represents represents an unsaturated heterocyclyl radical having 5 or 6 ring members and 1 to 3 heteroatoms which may optionally be mono- to trisubstituted by identical or different substituents from the group consisting of halogen, nitro, amino, hydroxyl;

in each case straight-chain or branched alkyl, alkoxy, alkylthio or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio or halogenoalkylsulphonyl having in each case 1 to 6 carbon atoms and 1 to 13 identical or different halogen atoms;

in each case straight-chain or branched alkylamino, dialkylamino, alkylcarbonyl, alkoxycarbonyl, hydroximinoalkyl or alkoximinoalkyl having in each case 1 to 6 carbon atoms in the individual alkyl moiety;

cycloalkyl having 3 to 6 carbon atoms;

and aryl, aryloxy, arylthio, arylalkyl, arylalkyloxy, arylalkylthio, heterocyclyl, heterocyclyloxy, heterocyclylthio, heterocyclylalkyl, heterocyclylalkyloxy or heterocyclylalkylthio, where these aromatic or heterocyclic radicals may be mono- to trisubstituted by identical or different substituents from the group consisting of halogen, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy or alkylthio having 1 to 4 carbon atoms, straight-chain or branched halogenoalkoxy or halogenoalkylthio having 1 to 4 carbon atoms and 1 to 9 identical or different halogen atoms.

$R^2$ preferably represents alkyl having 1 to 4 carbon atoms, alkenyl having 2 to 4 carbon atoms, halogenoalkyl having in each case 1 to 4 carbon atoms and 1 to 5 identical or different halogen atoms, halogenoalkenyl having in each case 2 to 4 carbon atoms and 1 to 5 identical or different halogen atoms or represents dialkylamino having in each case 1 to 4 carbon atoms in the two alkyl groups.

$R^2$ moreover preferably represents aryl having 6 to 10 carbon atoms which may be mono- to trisubstituted by identical or different substituents from the group consisting of nitro, halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms and halogenoalkylthio having 1 to 4 carbon atoms and 1 to 5 identical or different halogen atoms.

$R^2$ furthermore preferably represents a heterocyclyl radical having 5 or 6 ring members and 1 to 3 heteroatoms, such as nitrogen, oxygen and sulphur, where this radical may contain an oxo group and may be mono- to trisubstituted by identical or different substituents from the group consisting of halogen, cyano, nitro, amino, hydroxyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkylcarbonyl having 1 to 4 carbon atoms in the alkyl moiety, alkoxycarbonyl having 1 to 3 carbon atoms in the alkoxy moiety, carbamoyl, alkylaminocarbonyl having 1 to 4 carbon atoms in the alkyl moiety, dialkylaminocarbonyl having 1 to 4 carbon atoms in the individual alkyl moieties, hydroximinoalkyl or alkoximinoalkyl having in each case 1 to 4 carbon atoms in the individual alkyl moieties and cycloalkyl having 3 to 6 carbon atoms.

A particularly preferably represents a single bond or represents methanediyl, 1,1-ethanediyl, 1,2-ethanediyl 1,1-, 1,2-, 1,3- or 2,2-propanediyl, 1,1-, 1,2-, 1,3-, 1,4-, 2,2-, 2,3-butanediyl, 1,1-, 1,2- or 1,3-(2-methyl-propanediyl), 1,1-ethenediyl, 1,2-ethenediyl 1,1-, 1,2- or 1,3-propenediyl, ethinediyl, 1,3-propinediyl or a grouping —*O—$CH_2$—, —*O—$CH_2$—$CH_2$—, —*$CH_2$—O—, —*$CH_2$—O—$CH_2$—$CH_2$—, —*$CH_2$—S—, —*S—$CH_2$—, or where the atom labelled by * is in each case attached to $R^1$.

$R^3$ particularly preferably represents hydrogen or methyl.

$R^1$ particularly preferably represents hydrogen, or represents cyclopropyl, cyclobutyl, cyclopentyl, cyclohexyl, cyclopentenyl or cyclohexenyl, each of which is optionally mono- to trisubstituted by chlorine, methyl, ethyl, n- or i-propyl.

$R^1$ moreover particularly preferably represents phenyl which may be mono- to trisubstituted by identical or different substituents from the group consisting of fluorine, chlorine, bromine, nitro, carbamoyl, methyl, ethyl, n- or i-propyl, n-, i-, s- or t-butyl, methoxy, ethoxy, n- or i-propoxy, methylthio, ethylthio, n- or i-propylthio, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio or trifluoromethylsulphonyl, methylamino, ethylamino, n- or i-propylamino dimethylamino, diethylamino, acetyl, propionyl, methoxycarbonyl, ethoxycarbonyl, hydroximinomethyl, hydroximinoethyl, methoximinomethyl, ethoximinomethyl, methoximinoethyl and ethoximinoethyl, in each case doubly attached trimethylene (propane-1,3-diyl), methylenedioxy or ethylenedioxy, which is optionally mono- to tetrasubstituted by identical or different substituents from the group consisting of fluorine, chlorine, methyl and trifluoromethyl, cyclopropyl, cyclobutyl, cyclopentyl or cyclohexyl, and/or by phenyl, phenoxy, phenylthio, benzyl, benzyloxy, benzylthio, pyridyl, pyrimidinyl or thienyl, where these radicals may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy and trifluoroethoxy.

$R^1$ furthermore particularly preferably represents thienyl, furyl or pyridyl, where these radicals may be mono- to trisubstituted by identical or different substituents from the group consisting of fluorine, chlorine, bromine, nitro, amino, hydroxyl, methyl, ethyl, n- or i-propyl, n-, i-, s- or t-butyl, methoxy, ethoxy, n- or i-propoxy, methylthio, ethylthio, n- or i-propylthio, methylsulphonyl or ethylsulphonyl, trifluoromethyl, trifluoroethyl, difluoromethoxy, trifluoromethoxy, difluorochloromethoxy, trifluoroethoxy, difluoromethylthio, difluorochloromethylthio, trifluoromethylthio or trifluoromethylsulphonyl, methylamino, ethylamino, n- or i-propylamino, dimethylamino, diethylamino, acetyl, propionyl, methoxycarbonyl, ethoxycarbonyl, hydroximinomethyl, hydroximinoethyl, methoximinomethyl, ethoximinomethyl, methoximinoethyl or ethoximinoethyl, cyclopropyl, cyclobutyl, cyclopentyl and cyclohexyl, and/or by phenyl, phenoxy, phenylthio, benzyl, benzyloxy and/or benzylthio, where these aromatic radicals may be mono- to trisubstituted by identical or different substituents from the group consisting of fluorine, chlorine, bromine, nitro, methyl, ethyl, n- or i-propyl, n-, i-, s- or t-butyl, methoxy, ethoxy, n- or i-propoxy, methylthio, ethylthio, n- or i-propylthio, trifluoromethyl, trifluoroethyl, difluoromethoxy, trifluoromethoxy, difluorochloromethoxy, trifluoroethoxy, difluoromethylthio, difluorochloromethylthio and trifluoromethylthio.

$R^2$ particularly preferably represents methyl, ethyl, n- or i-propyl, n-, i-, s-, or t-butyl, dimethylamino or diethylamino.

$R^2$ moreover particularly preferably represents phenyl which may be mono- to trisubstituted by identical or different substituents from the group consisting of fluorine, chlorine, bromine, nitro, methyl, ethyl, methoxy, ethoxy, methylthio, ethylthio, trifluoromethyl, trifluoroethyl, difluoromethoxy, trifluoromethoxy, difluorochloromethoxy, trifluoroethoxy, difluoromethylthio, difluorochloromethylthio and trifluoromethylthio.

$R^2$ furthermore particularly preferably represents furyl, thienyl, oxazolyl, isoxazolyl, pyrazolyl, imidazolyl, thiazolyl, isothiazolyl, oxadiazolyl, thiadiazolyl, pyridinyl, pyridazinyl, pyrazinyl, 1,2,3-triazinyl, 1,2,4-triazinyl, 1,3,5-triazinyl, 1,2,4-triazolonyl, pyrrolidinyl, piperidinyl or morpholinyl, where these radicals may be mono-, di- or trisubstituted by identical or different substituents from the group consisting of fluorine, chlorine, bromine, cyano, nitro, amino, hydroxyl, carbamoyl, methyl, ethyl, n- or i-propyl, n-, i-, s-, or t-butyl, cyclopropyl, methoxy, ethoxy, n- or i-propoxy, trifluoromethyl, trifluoroethyl, difluoromethoxy, trifluoromethoxy, acetyl, propionyl, methoxycarbonyl, ethoxycarbonyl, hydroxyiminomethyl, hydroxyiminoethyl, methoxyiminomethyl, ethoxyiminomethyl, methoxyiminoethyl and ethoxyiminoethyl.

A very particularly preferably represents a single bond or represents methanediyl, 1,1-ethanediyl, 1,2-ethanediyl 1,1-, 1,2-, 1,3- or 2,2-propanediyl, 1,1-, 1,2-, 1,3-, 1,4-, 2,2-, 2,3-butanediyl, 1,1-, 1,2- or 1,3-(2-methyl-propanediyl), 1,2-ethenediyl,

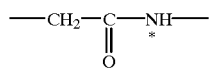

—*O—CH$_2$—CH$_2$—,  —*CH$_2$—O—,  —*CH$_2$—O—CH$_2$—CH$_2$—,  —*S—CH$_2$—,  —*CH$_2$—S— or

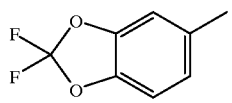

where the atom labelled by * is in each case attached to $R^1$.

$R^1$ very particularly preferably represents hydrogen or cyclohexenyl.

$R^1$ moreover very particularly preferably represents phenyl which is optionally mono- or disubstituted by fluorine, chlorine, bromine, methyl, ethyl, methoxy, nitro, trifluoromethyl, trifluoromethoxy, phenyl and/or phenoxy.

$R^1$ moreover very particularly preferably represents a radical of the formula

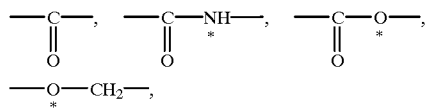

$R^1$ furthermore very particularly preferably represents thienyl, furyl or pyridyl.

$R^2$ very particularly preferably represents methyl, ethyl, n- or i-propyl, n-, i-, s-, or t-butyl, dimethylamino or diethylamino.

$R^2$ moreover very particularly preferably represents phenyl which is optionally mono- or disubstituted by fluorine, chlorine, bromine, nitro, methyl, ethyl and/or methoxy.

$R^2$ furthermore very particularly preferably represents furyl, thienyl, isoxazolyl, pyrazolyl, thiazolyl, imidazolyl, pyridyl or 1,2,4-triazolonyl which is optionally mono-, di- or trisubstituted by chlorine, bromine, amino, hydroxyl, methyl and/or cyclopropyl.

$R^2$ furthermore very particularly preferably represents pyrrolidinyl, piperidinyl or morpholinyl.

Some of the sulphonyloxadiazolones of the formula (I) which can be used according to the invention are known (cf. Zh. Org. Khim. 27 (1991), 1262–1270).

The sulphonyloxadiazolones of the formula

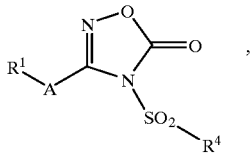

in which
A represents a single bond or represents alkanediyl, alkenediyl, alkinediyl or a grouping —*O—CH$_2$—, —*O—CH$_2$—CH$_2$—, —*CH$_2$—O—, —*CH$_2$—O—CH$_2$—CH$_2$—, —*CH$_2$—S—, —*S—CH$_2$—,

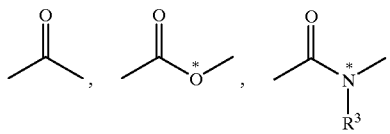

or

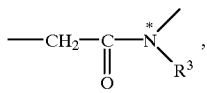

where the atom labelled by * is in each case attached to R$^1$ and
R$^3$ represents hydrogen or alkyl,
R$^1$ represents hydrogen, optionally substituted cycloalkyl, optionally substituted cycloalkenyl, optionally substituted aryl or optionally substituted heterocyclyl and
R$^4$ represents optionally substituted alkyl, optionally substituted alkenyl, dialkylamino, nitro-substituted phenyl which may also contain one or two further substituents, or represents optionally substituted heterocyclyl, but where R$^4$ does not represent propyl if A represents a direct bond and R$^1$ represents 2,4,6-trimethylphenyl
are novel.

The sulphonyloxadiazolones of the formula (Ia) can be prepared by reacting oxadiazolones of the formula

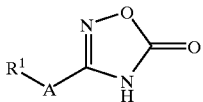

in which
A and R$^1$ are each as defined above, with sulphonyl halides of the formula

 (III)

in which
R$^4$ is as defined above and
X represents halogen,
if appropriate in the presence of an acid binder and if appropriate in the presence of a diluent.

The other compounds of the formula (I) can be prepared in the same manner.

The formula (Ia) provides a general definition of the novel sulphonyloxadiazolones. In this formula, A and R$^1$ each preferably have those meanings which have already been mentioned as being preferred for these radicals in connection with the description of the sulphonyloxadiazolones of the formula (I).

R$^4$ preferably represents alkyl having 1 to 4 carbon atoms, alkenyl having 2 to 4 carbon atoms, halogenoalkyl having in each case 1 to 4 carbon atoms and 1 to 5 identical or different halogen atoms, halogenoalkenyl having in each case 2 to 4 carbon atoms and 1 to 5 identical or different halogen atoms or represents dialkylamino having in each case 1 to 4 carbon atoms in the two alkyl groups, but where R$^4$ does not represent propyl if A represents a direct bond and R$^1$ represents 2,4,6-trimethyl-phenyl.

R$^4$ moreover preferably represents nitro-substituted phenyl which may additionally be mono- or disubstituted by identical or different substituents from the group consisting of nitro, halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms and halogenoalkylthio having 1 to 4 carbon atoms and 1 to 5 identical or different halogen atoms.

R$^4$ furthermore preferably represents a heterocyclyl radical having 5 or 6 ring members and 1 to 3 heteroatoms, such as nitrogen, oxygen and/or sulphur, where this radical may contain an oxo group and may be mono- to trisubstituted by identical or different substituents from the group consisting of halogen, cyano, nitro, amino, hydroxyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkylcarbonyl having 1 to 4 carbon atoms in the alkyl moiety, alkoxycarbonyl having 1 to 3 carbon atoms in the alkoxy moiety, carbamoyl, alkylaminocarbonyl having 1 to 4 carbon atoms in the alkyl moiety, dialkylaminocarbonyl having 1 to 4 carbon atoms in the individual alkyl moieties, hydroximinoalkyl or alkoximinoalkyl having in each case 1 to 4 carbon atoms in the individual alkyl moieties and cycloalkyl having 3 to 6 carbon atoms.

In the formula (Ia), A and R$^1$ particularly preferably represent those radicals which have already been mentioned as being particularly preferred for these radicals in connection with the description of the sulphonyloxadiazolones of the formula (Ia).

R$^4$ particularly preferably represents methyl, ethyl, n- or i-propyl, n-, i-, s-, or t-butyl, dimethylamino or diethylamino, but where R$^4$ does not represent n- or i-propyl if A represents a direct bond and R$^1$ represents 2,4,6-trimethylphenyl.

R$^4$ moreover particularly preferably represents nitro-substituted phenyl which may additionally be mono- or disubstituted by identical or different substituents from the group consisting of fluorine, chlorine, bromine, nitro, methyl, ethyl, methoxy, ethoxy, methylthio, ethylthio, trifluoromethyl, trifluoroethyl, difluoromethoxy, trifluoromethoxy, difluorochloromethoxy, trifluoroethoxy, difluoromethylthio, difluorochloromethylthio and trifluoromethylthio.

R$^4$ furthermore particularly preferably represents furyl, thienyl, oxazolyl, isoxazolyl, pyrazolyl, imidazolyl, thiazolyl, isothiazolyl, oxadiazolyl, thiadiazolyl, pyridinyl, pyridazinyl, pyrazinyl, 1,2,3-triazinyl, 1,2,4-triazinyl, 1,3,5-triazinyl, 1,2,4-triazolonyl, pyrrolidinyl, piperidinyl or morpholinyl, where these radicals may be mono-, di- or trisubstituted by identical or different substituents from the group consisting of fluorine, chlorine, bromine, cyano, nitro, amino, hydroxyl, carbamoyl, methyl, ethyl, n- or i-propyl, n-, i-, s-, or t-butyl, cyclopropyl, methoxy, ethoxy, n- or i-propoxy, trifluoromethyl, trifluoroethyl, difluoromethoxy, trifluoromethoxy, acetyl, propionyl, methoxycarbonyl, ethoxycarbonyl, hydroxyiminomethyl, hydroxyiminoethyl, methoxyiminomethyl, ethoxyiminomethyl, methoxyiminoethyl and ethoxyiminoethyl.

In the formula (Ia), A and $R^1$ each very particularly preferably represent those radicals which have already been mentioned as being very particularly preferred for these radicals in connection with the description of the sulphonyloxadiazolones of the formula (Ia).

$R^4$ very particularly preferably represents methyl, ethyl, n- or i-propyl, n-, i-, s-, or t-butyl, dimethylamino or diethylamino, but where $R^4$ does not represent n- or i-propyl if A represents a direct bond and $R^1$ represents 2,4,6-trimethylphenyl.

$R^4$ moreover very particularly preferably represents nitro-substituted phenyl which may additionally be substituted by fluorine, chlorine, bromine, nitro, methyl, ethyl or methoxy.

$R^4$ furthermore very particularly preferably represents furyl, thienyl, isoxazolyl, pyrazolyl, thiazolyl, imidazolyl, pyridyl or 1,2,4-triazolonyl, which is optionally mono-, di- or trisubstituted by chlorine, bromine, amino, hydroxyl, methyl and/or cyclopropyl.

$R^4$ furthermore very particularly preferably represents pyrrolidinyl, piperidinyl or morpholinyl.

Examples of substances according to the invention which may be mentioned are the sulphonyloxadiazolones listed in the tables below:

TABLE 1

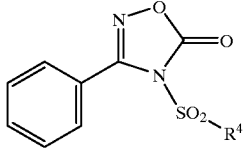
(I-b)

where $R^4$ represents the following substituents:

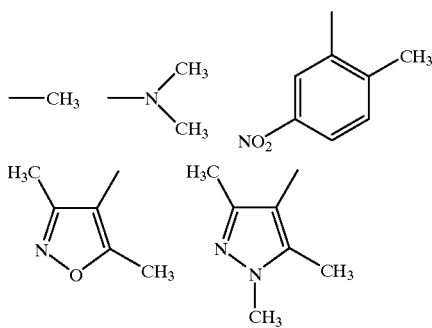

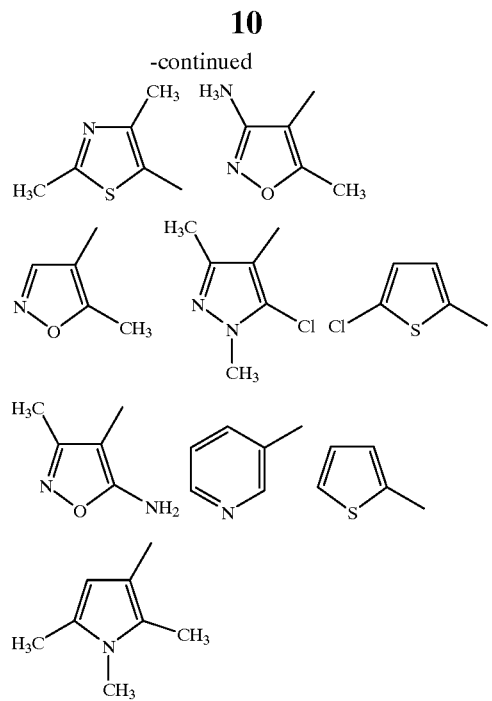

TABLE 2

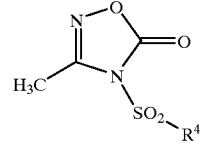
(I-c)

where $R^4$ represents the substituents mentioned in Table 1.

TABLE 3

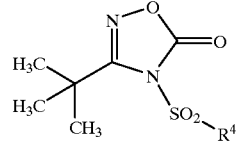
(I-d)

where $R^4$ represents the substituents mentioned in Table 1.

TABLE 4

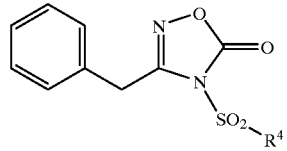
(I-e)

where R⁴ represents the substituents mentioned in Table 1.

TABLE 5

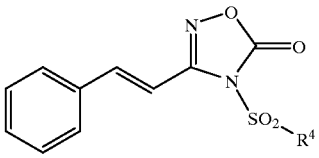

(I-f)

where R⁴ represents the substituents mentioned in Table 1.

TABLE 6

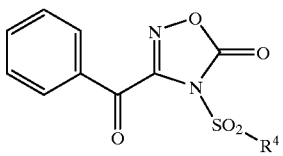

(I-g)

where R⁴ represents the substituents mentioned in Table 1.

TABLE 7

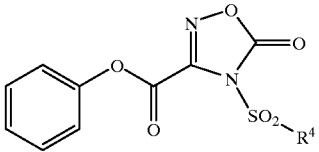

(I-h)

where R⁴ represents the substituents mentioned in Table 1.

TABLE 8

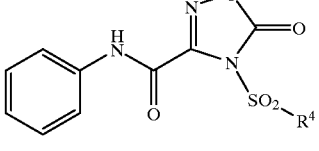

(I-i)

where R⁴ represents the substituents mentioned in Table 1.

TABLE 9

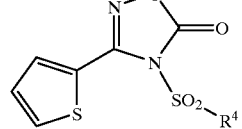

(I-j)

where R⁴ represents the substituents mentioned in Table 1.

TABLE 10

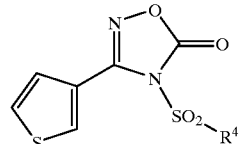

(I-k)

where R⁴ represents the substituents mentioned in Table 1.

TABLE 11

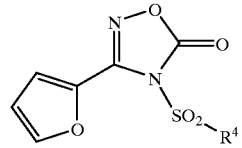

(I-l)

where R⁴ represents the substituents mentioned in Table 1.

TABLE 12

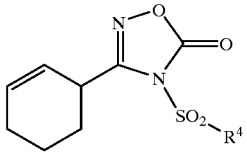

(I-m)

where R⁴ represents the substituents mentioned in Table 1.

TABLE 13

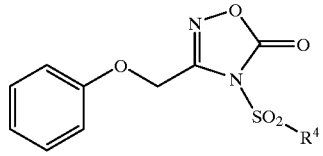

(I-n)

where R⁴ represents the substituents mentioned in Table 1.

Using, for example, 3-phenyl-4H-[1,2,4]oxadiazol-5-one and 3,5-dimethyl-isoxazole-4-sulphonyl chloride as starting materials, the course of the process according to the invention can be illustrated by the following scheme:

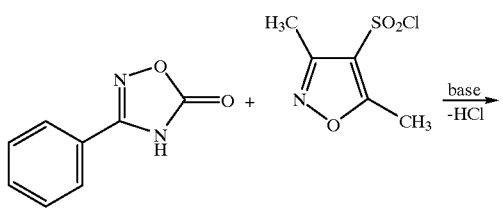

-continued

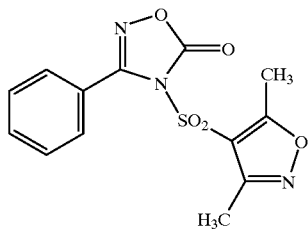

The formula (II) provides a general definition of the oxadiazolones required as starting materials for carrying out the process according to the invention. In this formula, A and $R^1$ preferably or particularly preferably have those meanings which have already been mentioned in connection with the description of the compounds of the formula (I) according to the invention as being preferred or as being particularly preferred for A and $R^1$.

The oxadiazolones of the formula (II) are known or can be prepared by known methods (cf. Synthesis 6, (1983), 483–486; J. Heterocyclic Chem. 10, (1973), 357–362; J. Org. Chem. 41, (1976), 3233; J. Heterocyclic Chem. 30 (5), (1993), 1253–1260).

The formula (III) provides a general definition of the sulphonyl halides furthermore required as reaction components for carrying out the process according to the invention. In this formula (III), $R^4$ preferably or particularly preferably has that meaning which has already been mentioned in connection with the description of the compounds of the formula (I-a) according to the invention as being preferred or as being particularly preferred for $R^4$. X preferably represents chlorine.

The sulphonyl halides of the formula (III) are known or can be prepared by known processes (J. Heterocyclic Chem. 1981, 997–1006).

Suitable diluents for carrying out the process according to the invention are all inert organic solvents. Preference is given to using aliphatic, alicyclic or aromatic hydrocarbons, such as petroleum ether, hexane, heptane, cyclohexane, methylcyclohexane, benzene, toluene, xylene or decalin; halogenated hydrocarbons, such as chlorobenzene, dichlorbenzene, dichloromethane, chloroform, tetrachloromethane, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; esters such as methyl acetate or ethyl acetate.

Suitable acid binders for carrying out the process according to the invention are all customary inorganic or organic bases. Preference is given to using alkaline earth metal or alkali metal hydrides, hydroxides, amides, alkoxides, acetates, carbonates or bicarbonates, such as sodium hydride, sodium amide, sodium methoxide, sodium ethoxide, potassium tert-butoxide, sodium hydroxide, potassium hydroxide, sodium acetate, potassium acetate, calcium acetate, sodium carbonate, potassium carbonate, potassium bicarbonate or sodium bicarbonate, furthermore ammonium compounds, such as ammonium hydroxide, ammonium acetate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

When carrying out the process according to the invention, the reaction temperatures can be varied within a relatively wide range. In general, the process is carried out at temperatures between 0° C. and 150° C., preferably between 20° C. and 120° C.

For carrying out the process according to the invention, generally from 1 to 2 mol, preferably from 1 to 1.3 mol, of the sulphonyl halide of the formula (III) and, if appropriate, from 1.0 to 2.0 mol, preferably from 1.0 to 1.3 mol, of acid acceptor are employed per mole of oxadiazolone of the formula (II).

The process according to the invention is generally carried out under atmospheric pressure. However, it is also possible to operate under elevated or reduced pressure—in general between 0.1 bar and 10 bar.

Work-up is carried out by customary methods.

The compounds which can be used according to the invention have potent microbicidal activity and can be employed for controlling undesirable microorganisms, such as fungi and bacteria, in crop protection and in the protection of materials.

Fungicides are employed in crop protection for controlling Plasmodiophoromycetes, Oomycetes, Chytridiomycetes, Zygomycetes, Ascomycetes, Basidiomycetes and Deuteromycetes.

Bactericides are employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above are mentioned as examples, but not by way of limitation:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;*

Pythium species, such as, for example, *Pythium ultimum;*

Phytophthora species, such as, for example, *Phytophthora infestans;*

Pseudoperonospora species, such as, for example, *Pseudoperonospora humuli* or *Pseudoperonospora cubensis;*

Plasmopara species, such as, for example, *Plasmopara viticola;*

Bremia species, such as, for example, *Bremia lactucae,*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea* (conidia form: Drechslera, syn: Helminthosporium);

Cochliobolus species, such as, for example, *Cochliobolus sativus* (conidia form: Drechslera, syn: Helminthosporium);

Uromyces species, such as, for example, *Uromyces appendiculatus;*

Puccinia species, such as, for example, *Puccinia recondita;*

Sclerotinia species, such as, for example, *Sclerotinia sclerotiorum;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*
Fusarium species, such as, for example, *Fusarium culmorum;*
Botrytis species, such as, for example, *Botrytis cinerea;*
Septoria species, such as, for example, *Septoria nodorum;*
Leptosphaeria species, such as, for example, *Leptosphaeria nodorum;*
Cercospora species, such as, for example, *Cercospora canescens;*
Alternaria species, such as, for example, *Alternaria brassicae;*
Pseudocercosporella species, such as, for example, *Pseudocercosporella herpotrichoides.*

The fact that the active compounds are well tolerated by plants at the concentrations required for controlling plant diseases permits the treatment of aerial parts of plants, of propagation stock and seeds, and of the soil.

The active compounds which can be used according to the invention can be employed particularly successfully for controlling diseases in fruit and vegetable growing and viticulture, such as, for example, against Phytophthora and Plasmopara species. They are also very successfully used for controlling cereal diseases, such as, for example, Leptosphaeria or Pyrenophora species, and also rice diseases, such as, for example, Pyricularia species.

Furthermore, the compounds which can be used according to the invention are also suitable for increasing the yield of crops. Moreover, they have reduced toxicity and they are well-tolerated by plants.

In the protection of materials, the compounds which can be used according to the invention can be employed for protecting industrial materials against infection with, and destruction by, undesired microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:
Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,* and
Staphylococcus, such as *Staphylococcus aureus.*

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. In the case of the use of water as an extender, organic solvents can, for example, also be used as auxiliary solvents. The following are mainly suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention can be used as such or in their formulations also mixed with known fungicides, bactericides, acaricides, nematicides or insecticides in order thus, for example, to widen the spectrum of action or to prevent development of resistance. In many cases, synergistic effects are achieved, i.e. the activity of the mixture exceeds the activity of the individual components.

Examples of co-components in mixtures are the following compounds:

Fungicides aldimorph, ampropylfos, ampropylfos potassium, andoprim, anilazine, azaconazole, azoxystrobin, benalaxyl, benodanil, benomyl, benzamacril, benzamacril-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulphamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulphocarb, methfuroxam, metiram, metomeclam, metsulphovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)ethanone-O-(phenylmethyl)-oxime, 1-(2-methyl-1-naphthalenyl)-1H-pyrrol-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole, 2',6'-dibromo-2-methyl-4'-trifluoromethoxy-4'-trifluoro-methyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-a-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrol-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethylmorpholinehydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide.
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
Bactericides
bromopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides
abamectin, acephate, acrinathrin, alanycarb, aldicarb, alphamethrin, amitraz, avermectin, AZ 60541, azadirachtin, azinphos A, azinphos M, azocyclotin,
Bacillus thuringiensis, 4-bromo-2-(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, BPMC, brofenprox, bromophos A, bufencarb, buprofezin, butocarboxim, butylpyridaben,
cadusafos, carbaryl, carbofuran, carbophenothion, carbosulphan, cartap, chloethocarb, chlorethoxyfos, chlorfenapyr, chlorfenvinphos, chlorfluazuron, chlormephos, N-[(6-chloro-3-pyridinyl)-methyl]-N-cyano-N-methyl-ethanimidamide, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton M, demeton S, demeton S-methyl, diafenthiuron, diazinon, dichlofenthion, dichlorvos, dicliphos, dicrotophos, diethion, diflubenzuron, dimethoate,
dimethylvinphos, dioxathion, disulphoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, fluazuron, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivermectin,
lambda-cyhalothrin, lufenuron,
malathion, mecarbam, mevinphos, mesulphenphos, metaldehyde, methacrifos, methamidophos, methidathion, methiocarb, methomyl, metolcarb, milbemectin, monocrotophos, moxidectin,
naled, NC 184, nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiophos, prothoate, pymetrozin, pyrachlophos, pyridaphenthion, pyresmethrin, pyrethrum, pyridaben, pyrimidifen, pyriproxifen,
quinalphos,
salithion, sebufos, silafluofen, sulphotep, sulprofos,
tebufenozide, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.

It is also possible to admix other known active compounds, such as herbicides, fertilizers and growth-promoting substances.

The active compounds can be used as such, in the form of their formulations or the use forms prepared therefrom, such as ready-to-use solutions, suspensions, wettable powders, pastes, soluble powders, dusts and granules. They are used in the customary manner, for example by pouring, spraying, atomizing, spreading, dusting, foaming, brushing on and the like. It is further possible to apply the active compounds by the ultra-low volume method or to inject the active compound formulation, or the active compound itself, into the soil. The seed of the plants can also be treated.

When the active compounds which can be used according to the invention are employed as fungicides, the application rates can be varied within a relatively wide range, depending on the form of application. In the treatment of parts of plants, the active compound application rates in the use forms are, in general, between 0.1 and 10,000 g/ha, preferably between 10 and 1000 g/ha. In the treatment of seed, application rates active compound of from 0.001 to 50 g, preferably 0.01 to 10 g, are generally required per kilogram of seed. In the treatment of the soil, active compound application rates of between 0.1 and 10,000 g/ha, preferably between 1 and 5000 g/ha, are employed.

The compositions used for the protection of industrial materials generally comprise an amount of 1 to 95% by weight, preferably 10 to 75% by weight, of the active compounds.

The use concentrations of the active compounds which can be used according to the invention depend on the species and the occurrence of the microorganisms to be controlled and on the composition of the material to be protected. The optimal rate of application can be determined by test series. In general, the use concentrations are in the range from 0.001 to 5% by weight, preferably 0.05 to 1.0% by weight, based on the material to be protected.

The activity and the activity spectrum of the active compounds to be used according to the invention in the protection of materials, or of the compositions, concentrates or quite generally formulations which can be prepared therefrom, can be increased by adding, if appropriate, other antimicrobially active compounds, fungicides, bactericides, herbicides, insecticides or other active compounds to widen the activity spectrum or to obtain particular effects, such as, for example, the additional protection against insects. These mixtures may have a broader activity spectrum than the compounds according to the invention.

The preparation and the use of active compounds which can be used according to the invention are illustrated by the examples below.

PREPARATION EXAMPLES

Example 1

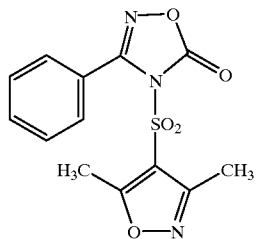

At room temperature, a mixture of 2.0 g (15 mmol) of 3-phenyl-4H-[1,2,4]oxadiazol-5-one and 30 ml absolute tetrahydrofuran is admixed with stirring with 0.40 g (10 mmol) of a suspension of sodium hydride (60% strength) and then stirred at room temperature for 10 minutes. 1.9 g (10 mmol) of 3,5-dimethylisoxazol-4-sulphonyl chloride are subsequently added, and the mixture is stirred at room temperature for another 20 hours. For work-up, the reaction mixture is poured into 150 ml of water. The resulting mixture is extracted twice with 80 ml of ethyl acetate each time. The combined organic phases are dried over sodium sulphate and concentrated under reduced pressure. The residue that remains is chromatographed over silica gel using methylene chloride as mobile phase. In this manner, 0.3 g (9% of theory) of 4-(3,5-dimethylisoxazole-4-sulphonyl)-3-phenyl-4H-[1,2,4]oxadiazol-5-one is obtained in the form of a colourless solid of melting point 90 to 95 C.

Example 2

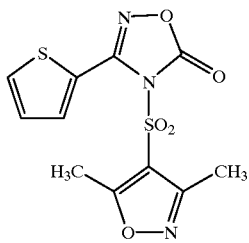

At room temperature, a mixture of 1.7 g (10 mmol) of 3-thiophen-2-yl-4H-[1,2,4]oxadiazol-5-one and 30 ml of absolute acetonitrile is admixed with stirring with 2.3 g (17 mmol) of powdered potassium carbonate. 1.0 g (5.5 mmol) 2.0 g (10 mmol) of 3,5-dimethylisoxazole-4-sulphonyl chloride are subsequently added, and the mixture is stirred at room temperature for another 20 hours. For work-up, the reaction mixture is poured into 150 ml of water. The resulting solid is filtered off, washed first with 10 ml of water and subsequently with 20 ml of diethyl ether and dried. This gives 1.77 g (57% of theory) of 4-(3,5-dimethylisoxazole-4-sulphonyl)-3-thiophen-2-yl-4H-[1,2,4]oxadiazol-5-one in the form of a yellow solid of melting point 138 C.

The sulphonyloxadiazolones of the formula (I) listed in Table 14 below are also prepared by the methods given above.

TABLE 14

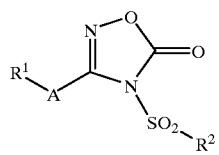

(I)

| Ex. No. | $R^1$ | A | $R^2$ | M(° C.) |
|---|---|---|---|---|
| 3 | phenyl | — | —NMe$_2$ | 92–96 |
| 4 | 3-chlorophenyl | — | H$_3$C–[isoxazole]–CH$_3$ | 160–164 |
| 5 | 3-chlorophenyl | — | —NMe$_2$ | 97–101 |
| 6 | 2-chlorophenyl | — | H$_3$C–[isoxazole]–CH$_3$ | 150–155 |

TABLE 14-continued (I)

[Structure: R¹–A–C(=N–O–)–N(SO₂R²)–C(=O) — 1,2,4-oxadiazol-5(4H)-one ring with R¹-A at 3-position and SO₂R² on N4]

| Ex. No. | R¹ | A | R² | M(° C.) |
|---|---|---|---|---|
| 7 | 4-chlorophenyl | — | 3,4-dimethyl-5-methylisoxazol-(yl) (3,4,5-trimethylisoxazole minus one methyl; H₃C-, CH₃ at 3,4 positions, H₃C at 5) | 155–156 |
| 8 | 4-chlorophenyl | — | 3-amino-4-methyl-5-methylisoxazolyl (4-methyl-5-methyl-3-amino-isoxazole) | 203–204 |
| 9 | phenyl | — | 3-amino-4-methyl-5-methylisoxazolyl | 193–194 |
| 10 | 2,4-dichlorophenyl | — | 3,4-dimethyl-5-methylisoxazolyl | 155–156 |
| 11 | phenyl | — | —CH₃ | 149–151 |
| 12 | phenyl | — | 2-methyl-5-nitrophenyl | 170–171 |
| 13 | phenyl | — | 3-cyclopropyl-4-methyl-5-methylisoxazolyl | 132–133 |
| 14 | 4-chlorophenyl | — | 2-methyl-5-nitrophenyl | 157–159 |
| 15 | 4-chlorophenyl | — | 3-cyclopropyl-4-methyl-5-methylisoxazolyl | 146–147 |
| 16 | 3-chlorophenyl | — | 3,4-dimethyl-5-methylisoxazolyl | 142–143 |
| 17 | 3-chlorophenyl | — | 3-amino-4-methyl-5-methylisoxazolyl | 153–154 |

TABLE 14-continued
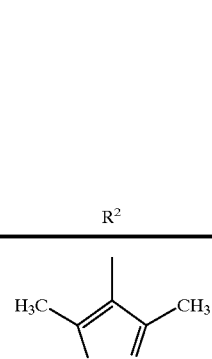
(I)
| Ex. No. | R¹ | A | R² | M(° C.) |
|---|---|---|---|---|
| 18 | 3,4-dichlorophenyl | — | 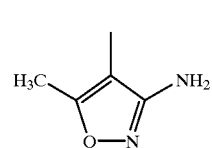 | 147–148 |
| 19 | 3,4-dichlorophenyl | — | 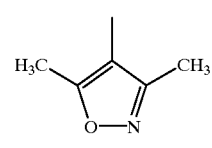 | 196–198 |
| 20 | 4-chloro-2-methylphenyl | — | 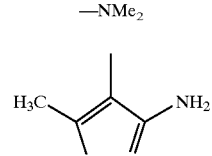 | 169–170 |
| 21 | 4-chloro-2-methylphenyl | — | —NMe₂ | 128–129 |
| 22 | 4-chloro-2-methylphenyl | — | 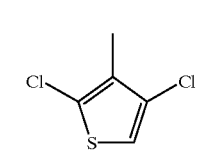 | 165–166 |
| 23 | 4-chlorophenyl | — | 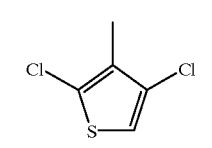 | 148–149 |
| 24 | phenyl | — | 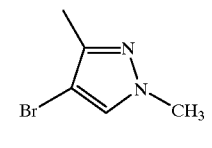 | 159–160 |
| 25 | phenyl | — | 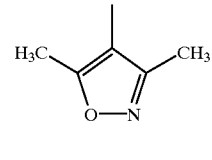 | 132–133 |
| 26 | 3-tolyl | — | 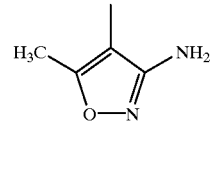 | 110–111 |
| 27 | 3-tolyl | — | 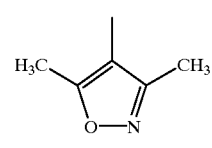 | 151–152 |

TABLE 14-continued (I)

$$R^1-A-\underset{\underset{SO_2-R^2}{|}}{\overset{N-O}{C}}=O$$

| Ex. No. | R¹ | A | R² | M(° C.) |
|---|---|---|---|---|
| 28 | 2-tolyl | — | 3,4,5-trimethylisoxazol-... (3,5-dimethyl-4-methyl-isoxazole) | 124–125 |
| 29 | 2-tolyl | — | —NMe₂ | 91–93 |
| 30 | 2-tolyl | — | 3-amino-4-methyl-5-methyl-isoxazole | 159–160 |
| 31 | 2-thienyl | — | 3-amino-4-methyl-5-methyl-isoxazole | 185–186 |
| 32 | 4-tolyl | — | 3,5-dimethyl-4-methyl-isoxazole | 146–148 |
| 33 | 4-trifluoromethyl-phenyl | — | 3,5-dimethyl-4-methyl-isoxazole | 157–158 |
| 34 | phenyl | —CH₂— | 3,5-dimethyl-4-methyl-isoxazole | 114–115 |
| 35 | 3-methylcyclohex-2-enyl | — | 3,5-dimethyl-4-methyl-isoxazole | 132–134 |
| 36 | 2-pyridyl | — | 3,5-dimethyl-4-methyl-isoxazole | 134–135 |

TABLE 14-continued
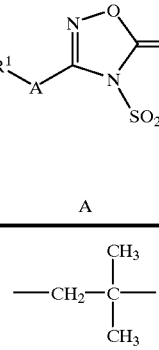
(I)
| Ex. No. | R¹ | A | R² | M(° C.) |
|---|---|---|---|---|
| 37 | H | —CH₂—C(CH₃)₃ | 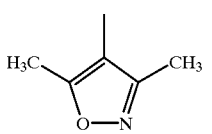 | 178–180 |
| 38 | 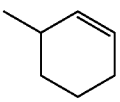 | — | 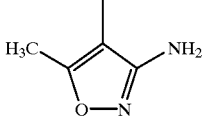 | 190–191 |
| 39 | 2-pyridyl | — | 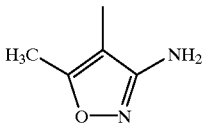 | 187–189 |
| 40 | H | —CH₂—C(CH₃)₃ | 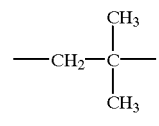 | 130–132 |
| 41 | 4-tolyl | — | 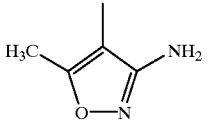 | 168–169 |
| 42 | 4-trifluoromethyl-phenyl | — | 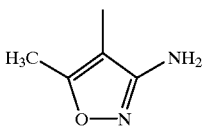 | 176–180 |
| 43 | phenyl | —CH₂— | 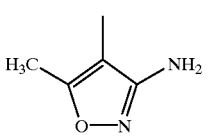 | 153–155 |
| 44 | 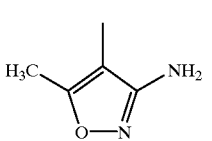 | — | 2-methyl-5-nitrophenyl | 185–188 |
| 45 | 2-pyridyl | — | 2-methyl-5-nitrophenyl | 183–185 |
| 46 | H | —CH₂—C(CH₃)₃ 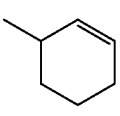 | 2-methyl-5-nitrophenyl | 181–182 |
| 47 | 4-tolyl | — | 2-methyl-5-nitrophenyl | 159–160 |

TABLE 14-continued

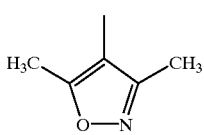

(I)

| Ex. No. | R¹ | A | R² | M(° C.) |
|---|---|---|---|---|
| 48 | 3-tolyl | — | 2-methyl-5-nitrophenyl | 149–151 |
| 49 | 2-tolyl | — | 2-methyl-5-nitrophenyl | 153–155 |
| 50 | 2-thienyl | — | 2-methyl-5-nitrophenyl | 178–180 |
| 51 | 4-trifluoromethyl-phenyl | — | 2-methyl-5-nitrophenyl | 127–129 |
| 52 | phenyl | —CH₂— | 2-methyl-5-nitrophenyl | 145–146 |
| 53 | 4-methoxyphenyl | —CH₂— | 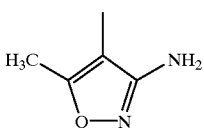 | 120–121 |
| 54 | 4-methoxyphenyl | —CH₂— | 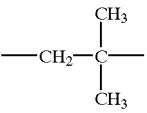 | 137–138 |
| 55 | 4-methoxyphenyl | —CH₂— | 2-methyl-5-nitrophenyl | 155–156 |
| 56 | 4-chlorophenyl | — | 2-thienyl | 141–142 |
| 57 | phenyl | — | 2-thienyl | 155–156 |
| 58 | 4-tolyl | — | 2-thienyl | 152–153 |
| 59 | 2-tolyl | — | 2-thienyl | 107–108 |
| 60 | H | 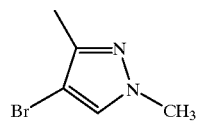 | 2-thienyl | 88–91 |
| 61 | 2-thienyl | — | 2-thienyl | 125–126 |
| 62 | 4-chlorophenyl | — | 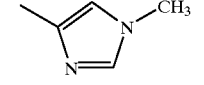 | 161–162 |
| 63 | 4-chlorophenyl | — | 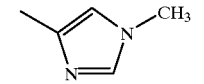 | 223–225 |
| 64 | phenyl | — | 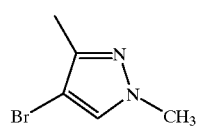 | 191–192 |
| 65 | 4-tolyl | — | 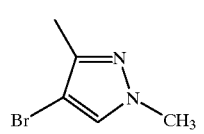 | 149–150 |
| 66 | 2-tolyl | — | 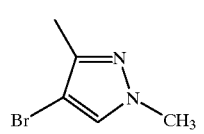 | 147–148 |

TABLE 14-continued (I)

| Ex. No. | R¹ | A | R² | M(° C.) |
|---|---|---|---|---|
| 67 | phenyl | —CH₂— | 4-bromo-1,3-dimethylpyrazol-5-yl | 134–135 |
| 68 | phenyl | —CH₂— | 2-thienyl | 119–121 |
| 69 | H | —CH₂—C(CH₃)₂—CH₃ | 4-bromo-1,3-dimethylpyrazol-5-yl | 104–105 |
| 70 | 4-methoxyphenyl | — | 3,4-dimethyl-5-methylisoxazol-... (3,4,5-trimethylisoxazolyl) | 161–162 |
| 71 | 4-methoxyphenyl | — | 3-amino-4-methyl-5-methylisoxazolyl | 217–219 |
| 72 | 4-methoxyphenyl | — | 2-methyl-5-nitrophenyl | 158–160 |
| 73 | 4-methoxyphenyl | — | 4-bromo-1,3-dimethylpyrazol-5-yl | 134–136 |
| 74 | 4-methoxyphenyl | — | 3,4,5-trimethylisoxazolyl | 161–162 |
| 75 | 4-methoxyphenyl | — | 3-amino-4-methyl-5-methylisoxazolyl | 217–219 |
| 76 | 4-methoxyphenyl | — | 2-methyl-5-nitrophenyl | 158–160 |
| 77 | 4-methoxyphenyl | — | 4-bromo-1,3-dimethylpyrazol-5-yl | 134–136 |
| 78 | 4-methoxyphenyl | — | 2-thienyl | 146–149 |

TABLE 14-continued
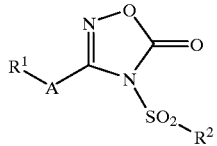
(I)
| Ex. No. | R[1] | A | R[2] | M(° C.) |
|---|---|---|---|---|
| 79 | 2,5-dichlorophenyl | — | 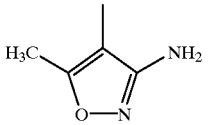 | 170–171 |
| 80 | 2,5-dichlorophenyl | — | —NMe$_2$ | 131–132 |
| 81 | 2,5-dichlorophenyl | — | 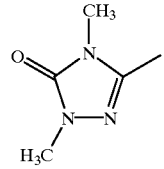 | 199–201 |
| 82 | 4-tolyl | — | 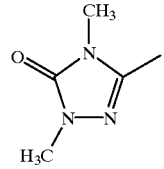 | 205–207 |
| 83 | phenyl | —CH$_2$— | 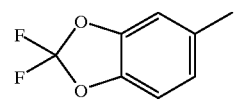 | 144–146 |
| 84 | 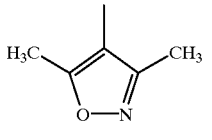 | — | 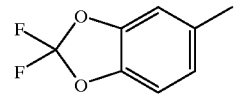 | 130–132 |
| 85 | 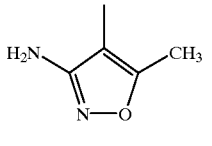 | — | 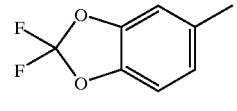 | 175–177 |
| 86 | 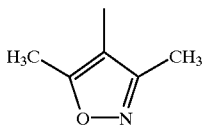 | — | 2-methyl-5-nitrophenyl | 164–166 |
| 87 | 2,4-dichlorophenyl | — |  | 162–163 |

TABLE 14-continued (I)

R¹—A—[3-oxo-1,2,4-oxadiazole]-N-SO₂R²

| Ex. No. | R¹ | A | R² | M(° C.) |
|---|---|---|---|---|
| 88 | 2,4-dichlorophenyl | — | 3-amino-4-methyl-5-methylisoxazole (H₂N, CH₃, CH₃) | 184–186 |
| 89 | 2-chlorophenyl | — | 3-amino-4-methyl-5-methylisoxazole | 171–172 |
| 90 | 2-trifluoromethylphenyl | — | 3,4,5-trimethylisoxazole | 151–152 |
| 91 | 2-trifluoromethylphenyl | — | 3-amino-4-methyl-5-methylisoxazole | 153–155 |
| 92 | 4-tolyl | — | 3-amino-4-methyl-5-methylisoxazole | 156–158 |
| 93 | 2,2-difluoro-5-methyl-benzo[1,3]dioxole | — | 3-amino-4-methyl-5-methylisoxazole | 222–225 |
| 94 | 3-methoxyphenyl | — | 3,4,5-trimethylisoxazole | 147–149 |
| 95 | 3-methoxyphenyl | — | 3-amino-4-methyl-5-methylisoxazole | 171–172 |
| 96 | H | CH(CH₃)₂CH₂ (isobutyl) | 3,4,5-trimethylisoxazole | 107–108 |

TABLE 14-continued

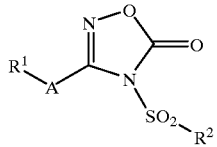
(I)

| Ex. No. | R¹ | A | R² | M(° C.) |
|---|---|---|---|---|
| 97 | H | 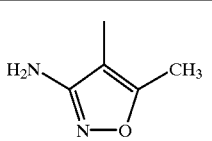 CH₃ | 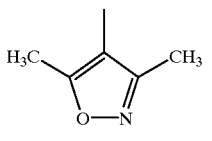 H₂N, CH₃, CH₃ isoxazole | 182–183 |
| 98 | 3-trifluoromethylphenyl | — | 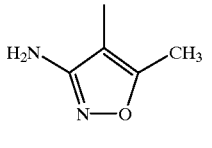 H₃C, CH₃, CH₃ isoxazole | 167–168 |
| 99 | 3-trifluoromethylphenyl | — | 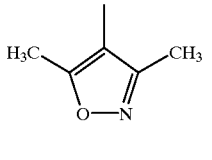 H₂N, CH₃, CH₃ isoxazole | 165–167 |
| 100 | 2-fluorophenyl | — | 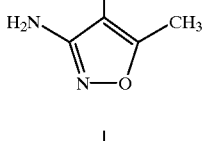 H₃C, CH₃, CH₃ isoxazole | 108–110 |
| 101 | 2-fluorophenyl | — | 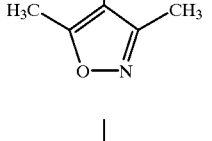 H₂N, CH₃, CH₃ isoxazole | 153–154 |
| 102 | 3-fluorophenyl | — | 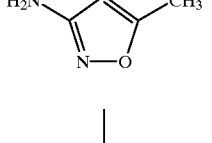 H₃C, CH₃, CH₃ isoxazole | 109–110 |
| 103 | 3-fluorophenyl | — | 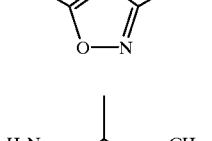 H₂N, CH₃, CH₃ isoxazole | 169–170 |
| 104 | 4-fluorophenyl | — | 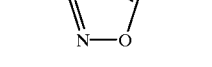 H₃C, CH₃, CH₃ isoxazole | 130–132 |
| 105 | 4-fluorophenyl | — | H₂N, CH₃, CH₃ isoxazole | 204–206 |

TABLE 14-continued

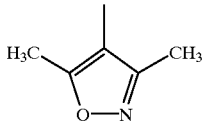

(I)

| Ex. No. | R[1] | A | R[2] | M(° C.) |
|---|---|---|---|---|
| 106 | 2-methoxyphenyl | — | 3,5-dimethylisoxazol-4-yl | 169–170 |
| 107 | 2-methoxyphenyl | — | 3-amino-5-methylisoxazol-4-yl | 195–197 |
| 108 | phenyl | —*O—CH$_2$— | 3,5-dimethylisoxazol-4-yl | 126–128 |
| 109 | phenyl | —*O—CH$_2$— | 3-amino-5-methylisoxazol-4-yl | 169–171 |
| 110 | 4-phenoxyphenyl | — | 3,5-dimethylisoxazol-4-yl | 128–130 |
| 111 | 4-phenoxyphenyl | — | 3-amino-5-methylisoxazol-4-yl | 182–184 |
| 112 | 3-methoxyphenyl | —CH$_2$— | 3,5-dimethylisoxazol-4-yl | 121–122 |
| 113 | 3-methoxyphenyl | —CH$_2$— | 3-amino-5-methylisoxazol-4-yl | 115–116 |
| 114 | 3-nitrophenyl | — | 3,5-dimethylisoxazol-4-yl | 179–181 |

TABLE 14-continued (I)

| Ex. No. | R¹ | A | R² | M(° C.) |
|---|---|---|---|---|
| 115 | 3-nitrophenyl | — | 3-amino-4-methyl-5-methyl-isoxazolyl (H₂N, CH₃, CH₃) | 191–193 |
| 116 | 2-nitrophenyl | — | 3,5-dimethyl-4-methyl-isoxazolyl (H₃C, CH₃, CH₃) | 212–213 |
| 117 | 2-nitrophenyl | — | 3-amino-4-methyl-5-methyl-isoxazolyl (H₂N, CH₃, CH₃) | 195–196 |
| 118 | 4-nitrophenyl | — | 3,5-dimethyl-4-methyl-isoxazolyl (H₃C, CH₃, CH₃) | 209–211 |
| 119 | 4-nitrophenyl | — | 3-amino-4-methyl-5-methyl-isoxazolyl (H₂N, CH₃, CH₃) | 230–231 |
| 120 | 2-trifluoromethylphenyl | — | 3,5-dimethyl-4-methyl-isoxazolyl (H₃C, CH₃, CH₃) | 162–163 |
| 121 | 2-trifluoromethylphenyl | — | 3-amino-4-methyl-5-methyl-isoxazolyl (H₂N, CH₃, CH₃) | 164–165 |
| 122 | 3-trifluoromethoxyphenyl | — | 3,5-dimethyl-4-methyl-isoxazolyl (H₃C, CH₃, CH₃) | 145–146 |
| 123 | 3-trifluoromethoxyphenyl | — | 3-amino-4-methyl-5-methyl-isoxazolyl (H₂N, CH₃, CH₃) | 133–135 |

TABLE 14-continued (I)

| Ex. No. | R¹ | A | R² | M(° C.) |
|---|---|---|---|---|
| 124 | 4-phenylphenyl | — | 3,5-dimethylisoxazol-4-yl | 107–108 |
| 125 | 4-phenylphenyl | — | 3-amino-5-methylisoxazol-4-yl | 103–104 |
| 126 | phenyl | —*NH—CO—CH₂— | 3,5-dimethylisoxazol-4-yl | 152–154 |
| 127 | phenyl | —*NH—CO—CH₂— | 3-amino-5-methylisoxazol-4-yl | 196–197 |
| 128 | 4-chlorophenyl | —*NH—CO—CH₂— | 3,5-dimethylisoxazol-4-yl | 167–169 |
| 129 | 4-chlorophenyl | —*NH—CO—CH₂— | 3-amino-5-methylisoxazol-4-yl | 188–190 |
| 130 | 4-tolyl | —CH₂— | 3,5-dimethylisoxazol-4-yl | 129–130 |
| 131 | 4-tolyl | —CH₂— | 3-amino-5-methylisoxazol-4-yl | 153–155 |
| 132 | 4-chlorophenyl | —CH₂— | 3,5-dimethylisoxazol-4-yl | 101–102 |

TABLE 14-continued (I)

*[Structure: 1,2,4-oxadiazol-5(4H)-one with R¹-A- at position 3 and -SO₂-R² at position 4]*

| Ex. No. | R¹ | A | R² | M(° C.) |
|---|---|---|---|---|
| 133 | 4-chlorophenyl | —CH₂— | 3-amino-4,5-dimethylisoxazole (H₂N on C3) | 149–150 |
| 134 | H | —*CH₂—O—CH₂—CH₂— | 3,5-dimethyl-4-yl isoxazole | 72–73 |
| 135 | H | —*CH₂—O—CH₂—CH₂— | 3-amino-4,5-dimethylisoxazole | 94–96 |
| 136 | H | —*O—CH₂—CH₂— | 3,5-dimethyl-4-yl isoxazole | logP = 0.67 |
| 137 | H | —*O—CH₂—CH₂— | 3-amino-4,5-dimethylisoxazole | logP = 1.09 |
| 138 | 3-tolyl | —CH₂— | 3,5-dimethyl-4-yl isoxazole | 114–115 |
| 139 | 3-tolyl | —CH₂— | 3-amino-4,5-dimethylisoxazole | 127–128 |
| 140 | 3-chlorophenyl | —CH₂— | 3,5-dimethyl-4-yl isoxazole | 136–137 |
| 141 | 3-chlorophenyl | —CH₂— | 3-amino-4,5-dimethylisoxazole | 151–152 |

TABLE 14-continued $$\underset{R^1}{\overset{}{\diagdown}}A\underset{}{\overset{N-O}{\underset{N}{\diagup}}}\underset{SO_2}{\overset{}{\diagdown}}R^2 \quad (I)$$

| Ex. No. | R¹ | A | R² | M(° C.) |
|---|---|---|---|---|
| 142 | 3,4-dichlorophenyl | —CH₂— | (3-amino-4-methyl-5-methylisoxazol-4-yl) | 138–139 |
| 143 | 4-trifluoromethylphenyl | —CH₂— | (3-amino-4-methyl-5-methylisoxazol-4-yl) | 179–180 |
| 144 | 2-tolyl | —*O—CH₂— | —NMe₂ | **) |
| 145 | 2-chlorophenyl | —*O—CH₂— | —NMe₂ | logP = 3.03 |
| 146 | 2-chloro-4-trifluoromethylphenyl | —*O—CH₂— | —NMe₂ | logP = 3.68 |

The atoms labelled with * are in each case attached to R¹
**) The compound was characterized by the ¹H NMR spectrum (300 MHz, TMS). δ = 2.25 (s, 3H); 2.82 (s, 3H); 3.15 (s, 3H) ppm.

In the Table 14 Me represents methyl.

The log P values were determined in accordance with EEC Directive 79/831 Annex V,A8 using HPLC (gradient method, acetonitrile/0.1% aqueous phosphoric acid).

Use Examples

Example A

Phytophthora test (tomato)/protective

Solvent: 47 parts by weight of acetone

Emulsifier: 3 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of Phytophthora infestans. The plants are then placed in an incubation cabin at approximately 20 C. and 100% relative atmospheric humidity.

Evaluation is carried out 3 days after the inoculation. 0% represents an efficacy which corresponds to that of the control, whereas an efficacy of 100% means that no infection is observed.

Active compounds, application rates and test results are shown in the table below.

TABLE A

Phytophthora test (tomato)/protective

| Active compound | Active compound application rate in g/ha | Efficacy in % |
|---|---|---|
| According to the invention | | |
| (4) | 50 | 94 |
| (6) | 50 | 98 |

TABLE A-continued

Phytophthora test (tomato)/protective

| Active compound | Active compound application rate in g/ha | Efficacy in % |
|---|---|---|
| (7) | 50 | 97 |
| (8) | 50 | 97 |
| (9) | 50 | 93 |
| (17) | 50 | 98 |
| (19) | 50 | 99 |
| (20) | 50 | 100 |
| (21) | 50 | 100 |
| (22) | 50 | 96 |

TABLE A-continued

Phytophthora test (tomato)/protective

| Active compound | Active compound application rate in g/ha | Efficacy in % |
|---|---|---|
| (23) | 50 | 95 |
| (26) | 50 | 96 |
| (27) | 50 | 99 |
| (28) | 50 | 97 |
| (2) | 50 | 97 |
| (32) | 50 | 99 |
| (33) | 50 | 99 |
| (34) | 50 | 99 |

TABLE A-continued

Phytophthora test (tomato)/protective

| Active compound | Active compound application rate in g/ha | Efficacy in % |
|---|---|---|
| (35) | 50 | 99 |
| (36) | 50 | 93 |
| (37) | 50 | 96 |
| (38) | 50 | 96 |
| (40) | 50 | 94 |
| (41) | 50 | 97 |
| (42) | 50 | 94 |
| (43) | 50 | 95 |
| (46) | 50 | 98 |

TABLE A-continued

Phytophthora test (tomato)/protective

| Active compound | Active compound application rate in g/ha | Efficacy in % |
|---|---|---|
| (55) | 50 | 90 |
| (70) | 50 | 96 |
| (71) | 50 | 95 |
| (79) | 50 | 97 |
| (84) | 50 | 99 |
| (85) | 50 | 94 |
| (90) | 50 | 96 |
| (94) | 50 | 90 |

TABLE A-continued

Phytophthora test (tomato)/protective

| Active compound | Active compound application rate in g/ha | Efficacy in % |
|---|---|---|
| (99) | 50 | 94 |
| (100) | 50 | 96 |
| (102) | 50 | 99 |
| (104) | 50 | 98 |
| (105) | 50 | 98 |
| (109) | 50 | 94 |
| (112) | 50 | 96 |
| (118) | 50 | 93 |

TABLE A-continued
Phytophthora test (tomato)/protective
| Active compound | Active compound application rate in g/ha | Efficacy in % |
|---|---|---|
| 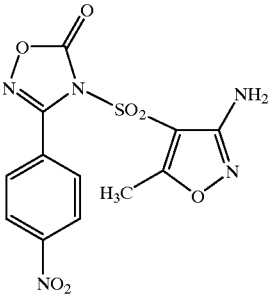 (119) | 50 | 94 |
| 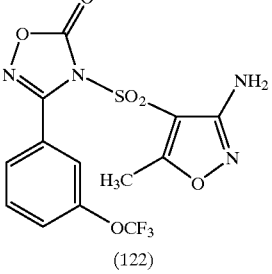 (122) | 50 | 100 |
| 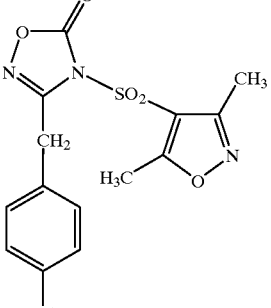 (132) | 50 | 94 |
| 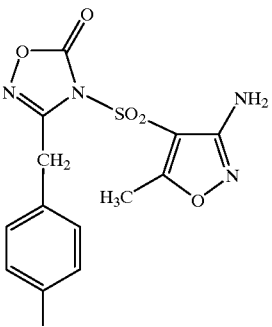 (133) | 50 | 94 |
| 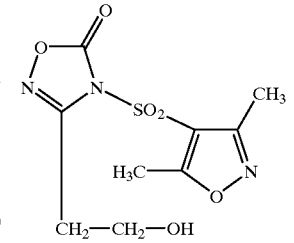 (136) | 50 | 91 |
| 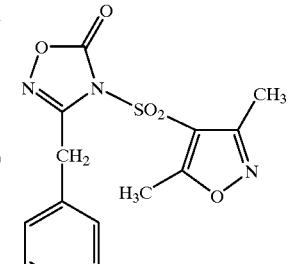 (138) | 50 | 99 |
| 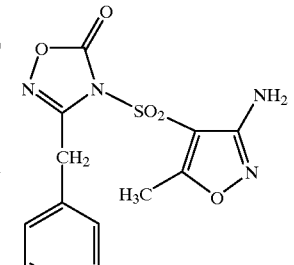 (139) | 50 | 96 |
| 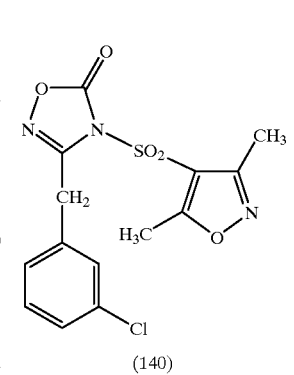 (140) | 50 | 96 |

TABLE A-continued

Phytophthora test (tomato)/protective

| Active compound | Active compound application rate in g/ha | Efficacy in % |
|---|---|---|
| (141) | 50 | 94 |
| (142) | 50 | 99 |

Example B

Plasmopara test (grapevine)/protective

Solvent: 47 parts by weight of acetone

Emulsifier: 3 parts by weight alkylaryl polyglycol ether

To produce a suitable preparation of active compound, 1 part by weight of active compound is mixed with the stated amounts of solvent and emulsifier and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at approximately 20 C. and 100% relative atmospheric humidity for 1 day. The plants are subsequently placed in a greenhouse at approximately 21 C. and approximately 90% relative atmospheric humidity for 5 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

Active compounds, application rates and test results are shown in the table below.

TABLE B

Plasmopara test (grapevine)/protective

| Active compound | Active compound application rate in g/ha | Efficacy in % |
|---|---|---|
| According to the invention | | |
| (8) | 50 | 93 |
| (17) | 50 | 97 |
| (19) | 50 | 100 |
| (20) | 50 | 99 |

TABLE B-continued

Plasmopara test (grapevine)/protective

| Active compound | Active compound application rate in g/ha | Efficacy in % |
|---|---|---|
| 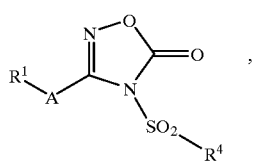 (22) | 50 | 99 |

What is claimed is:

1. A sulphonyloxadiazolone of the formula

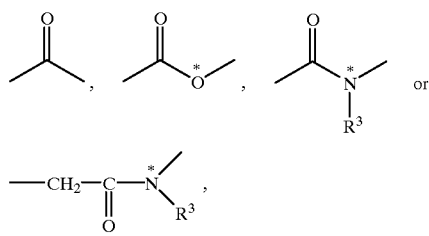

(Ia)

in which

A represents a single bond or represents alkanediyl, alkenediyl, alkinediyl or a grouping —*O—CH$_2$—, —*O—CH$_2$—CH$_2$—, —*CH$_2$—O—, —*CH$_2$—O—CH$_2$—CH$_2$—, —*CH$_2$—S—, —*S—CH$_2$—,

 or

—CH$_2$—C(=O)—N(*)—R$^3$ , where the atom labeled by * is in each case attached to R$^1$ and R$^3$ represents hydrogen or an alkyl group, R$^1$ represents hydrogen, an optionally substituted cycloalkyl group, an optionally substituted cycloalkenyl group, an optionally substituted aryl group or an optionally substituted heterocyclic group and R$^4$ represents an optionally substituted alkyl group, an optionally substituted alkenyl group, a dialkylamino group, a nitro-substituted phenyl group which may also contain one or two further substituents, or represents optionally a substituted heterocyclic group, provided that R$^4$ does not represent propyl when A represents a direct bond and R$^1$ represents a 2,4,6-trimethyl-phenyl group.

2. A process for preparing a sulphonyloxadiazolone of the formula (Ia) according to claim 1 comprising reacting an oxadiazolone of the formula

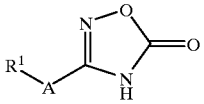

(II)

in which

A and R$^1$ are as defined in claim 1, with a sulphonyl halide of the formula

R$^4$—SO$_2$—X        (III)

in which

R$^4$ is as defined in claim 1 and

X represents halogen, optionally in the presence of an acid binder and optionally, in the presence of a diluent.

3. A microbicidal composition comprising a microbicidally effective amount of at least one sulphonyloxadiazolone of the formula (Ia) of claim 1, and an extender and/or surfactant.

4. A sulphonyloxadiazolone according to claim 1 represented by the formula

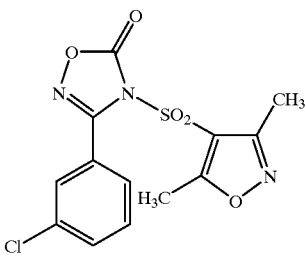

5. A sulphonyloxadiazolone according to claim 1 represented by the formula

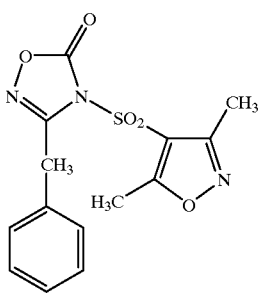

6. A sulphonyloxadiazolone according to claim 1 represented by the formula

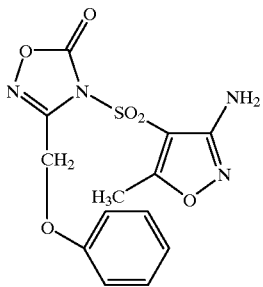

7. A method for controlling undesirable microorganisms comprising applying a microbicidally effective amount of a sulphonyloxadiazolone of the formula

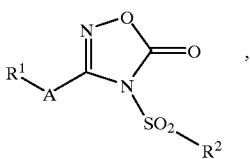
(I)

in which

A represents a single bond or represents a dialkyl group, a dialkenyl group, a dialkynyl group or a grouping —*O—CH$_2$—, —*O—CH$_2$—CH$_2$—, —*CH$_2$—O—, —*CH$_2$—O—CH$_2$—CH$_2$—, —*CH$_2$—S—, —*S—CH$_2$—,

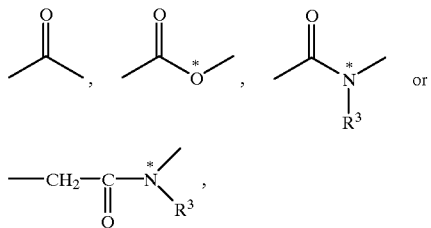

where the atom labelled by * is in each case attached to R$^1$ and

R$^3$ represents hydrogen or an alkyl group,

R$^1$ represents hydrogen, an optionally substituted cycloalkyl group, an optionally substituted cycloalkenyl group, an optionally substituted aryl group or an optionally substituted heterocyclic group and R$^2$ represents, in each case; an optionally substituted alkyl, alkenyl, dialkylamino, aryl or heterocyclic group, to the undesirable microorganisms and/or their habitat.

8. The method of claim 7 in which a sulphonyloxadiazolone of the formula (I) in which A represents a single bond or represents a dialkyl group having 1 to 4 carbon atoms, a dialkenyl group having 2 to 4 carbon atoms, a dialkynyl group having 2 to 4 carbon atoms or a grouping —*O—CH$_2$—, —*O—CH$_2$—CH$_2$—, —*CH$_2$—, —*CH$_2$—O—CH$_2$—CH$_2$—, —*CH$_2$—S—, —*S—CH$_2$—,

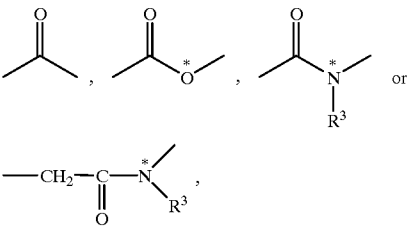

where the atom labeled by * is in each case attached to R$^1$,

R$^3$ represents hydrogen or an alkyl group having 1 to 4 carbon atoms,

R$^1$ represents hydrogen, or a cycloalkyl group having 3 to 8 carbon atoms or a cycloalkenyl group having 3 to 8 carbon atoms, each of which is optionally mono- to trisubstituted by identical or different substituents selected from the group consisting of halogen and alkyl having 1 to 3 carbon atoms, or R$^1$ represents an aryl radical having 6 to 10 carbon atoms, where each of these radicals may be mono- to trisubstituted by identical or different substituents selected from the group consisting of halogen, nitro, carbamoyl;

in each case, straight-chain or branched alkyl, alkoxy, alkylthio or alkylsulphonyl having in each case 1 to 6 carbon atoms;

in each case, straight-chain or branched alkenyl or alkenyloxy having in each case 2 to 6 carbon atoms;

in each case, straight-chain or branched halogenoalkyl, halogenoalkoxy, halogenoalkylthio or halogenoalkylsulphonyl having in each case 1 to 6 carbon atoms and 1 to 5 identical or different halogen atoms;

in each case, straight-chain or branched halogenoalkenyl or halogenoalkenyloxy having in each case 2 to 6 carbon atoms and 1 to 5 identical or different halogen atoms;

in each case, straight-chain or branched alkylamino, dialkylamino, alkylcarbonyl, alkoxycarbonyl, hydroximinoalkyl or alkoximinoalkyl having in each case 1 to 6 carbon atoms in the individual alkyl moieties;

in each case, doubly attached alkylene or dioxyalkylene having in each case 1 to 6 carbon atoms and being in each case optionally mono- to tetrasubstituted by identical or different substituents selected from the group consisting of halogen, straight-chain or branched alkyl having from 1 to 4 carbon atoms and straight-chain or branched halogenoalkyl having 1 to 4 carbon atoms and 1 to 5 identical or different halogen atoms;

cycloalkyl having 3 to 6 carbon atoms;

and aryl, aryloxy, arylthio, arylalkyl, arylalkyloxy, arylalkylthio, heterocyclic, heterocyclyloxy, heterocyclylthio, heterocyclylalkyl, heterocyclylalkyloxy or heterocyclylalkylthio, where these aromatic or heterocyclic radicals may be mono- to trisubstituted by identical or different substituents from the group consisting of halogen, nitro, straight-chain or branched alkyl having 1 to 4 carbon atoms, straight-chain or branched halogenoalkyl having 1 to 4 carbon atoms and 1 to 5 identical or different halogen atoms, straight-chain or branched alkoxy or alkylthio having 1 to 4 carbon atoms, and straight-chain or branched halogenoalkoxy having 1 to 4 carbon atoms and 1 to 9 identical or different halogen atoms, or $R^1$ represents an unsaturated heterocyclic radical having 5 or 6 ring members and 1 to 3 heteroatoms which may optionally be mono- to trisubstituted by identical or different substituents selected from the group consisting of halogen, nitro, amino, hydroxyl;

in each case straight-chain or branched alkyl, alkoxy, alkylthio or alkylsulphonyl having in each case 1 to 6 carbon atoms;

in each case straight-chain or branched alkenyl or alkenyloxy having in each case 2 to 6 carbon atoms;

in each case straight-chain or branched halogenoalkyl, halogenoalkoxy, halogenoalkylthio or halogenoalkylsulphonyl having in each case 1 to 6 carbon atoms and 1 to 13 identical or different halogen atoms;

in each case straight-chain or branched alkylamino, dialkylamino, alkylcarbonyl, alkoxycarbonyl, hydroximinoalkyl or alkoximinoalkyl having in each case 1 to 6 carbon atoms in the individual alkyl moieties;

cycloalkyl having 3 to 6 carbon atoms;

and aryl, aryloxy, arylthio, arylalkyl, arylalkyloxy, arylalkylthio, heterocyclic, heterocyclyloxy, heterocyclylthio, heterocyclylalkyl, heterocyclylalkyloxy or heterocyclylalkylthio, where these aromatic or heterocyclic radicals may be mono- to trisubstituted by identical or different substituents selected from the group consisting of halogen, nitro, straight-chain or branched alkyl having 1 to 4 carbon atoms, straight-chain or branched halogenoalkyl having 1 to 4 carbon atoms and 1 to 9 identical or different halogen atoms, straight-chain or branched alkoxy or alkylthio having 1 to 4 carbon atoms, straight-chain or branched halogenoalkoxy or halogenoalkylthio having 1 to 4 carbon atoms and 1 to 9 identical or different halogen atoms, and $R^2$ represents an alkyl group having 1 to 4 carbon atoms, an alkenyl group having 2 to 4 carbon atoms, a halogenoalkyl group having in each case 1 to 4 carbon atoms and 1 to 5 identical or different halogen atoms, a halogenoalkenyl group having in each case 2 to 4 carbon atoms and 1 to 5 identical or different halogen atoms or represents dialkylamino having in each case 1 to 4 carbon atoms in the two alkyl groups, or $R^2$ represents an aryl group having 6 to 10 carbon atoms which may be mono- to trisubstituted by identical or different substituents selected from the group consisting of nitro, halogen, alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms and halogenoalkylthio having 1 to 4 carbon atoms and 1 to 5 identical or different halogen atoms, or $R^2$ represents a heterocyclic radical having 5 or 6 ring members and 1 to 3 heteroatoms, where this radical may contain an oxo group and may be mono- to trisubstituted by identical or different substituents selected from the group consisting of halogen, cyano, nitro, amino, hydroxyl, alkyl having 1 to 4 carbon atoms, alkoxy having 1 to 4 carbon atoms, halogenoalkyl having 1 to 4 carbon atoms and 1 to 5 identical or different halogen atoms, halogenoalkoxy having 1 to 4 carbon atoms and 1 to 5 identical or different halogen atoms, alkylcarbonyl having 1 to 4 carbon atoms in the alkyl moiety, alkoxycarbonyl having 1 to 3 carbon atoms in the alkoxy moiety, carbamoyl, alkylaminocarbonyl having 1 to 4 carbon atoms in the alkyl moiety, dialkylaminocarbonyl having 1 to 4 carbon atoms in the individual alkyl moieties, hydroximinoalkyl or alkoximinoalkyl having in each case 1 to 4 carbon atoms in the individual alkyl moieties and cycloalkyl having 3 to 6 carbon atoms is used.

* * * * *